United States Patent
Harrigan (12)

(10) Patent No.: US 10,561,513 B1
(45) Date of Patent: Feb. 18, 2020

(54) BRACE WITH REMOVABLE AROMATHERAPY POUCH

(71) Applicant: Jahumi Harrigan, New York, NY (US)

(72) Inventor: Jahumi Harrigan, New York, NY (US)

(*) Notice: Subject to any disclaimer, the term of this patent is extended or adjusted under 35 U.S.C. 154(b) by 384 days.

(21) Appl. No.: 15/443,408

(22) Filed: Feb. 27, 2017

(51) Int. Cl.
A61F 7/02 (2006.01)
A61F 5/01 (2006.01)
A61F 5/02 (2006.01)

(52) U.S. Cl.
CPC .......... *A61F 5/0111* (2013.01); *A61F 5/0106* (2013.01); *A61F 5/0118* (2013.01); *A61F 5/02* (2013.01); *A61F 7/02* (2013.01); *A61F 2007/0207* (2013.01); *A61F 2007/0225* (2013.01)

(58) Field of Classification Search
CPC ............... A61F 7/02; A61F 2007/0207; A61F 2007/0223; A61F 2007/0279; A61F 2007/0266; A61F 2007/0088; A61F 5/0111; A61F 5/0106; A61F 5/01; A61F 2007/023; A61F 2013/00187; A61F 2007/0001; A61F 2007/0086; A61F 7/10; A61F 13/0203; A61F 2007/0295; A61F 2013/002; A61F 13/0213; A61F 2007/0056; A61F 7/00; A61F 7/106; A61F 2007/0098; A61F 2013/0017; A61F 2013/00519; A61F 7/03; A61F 2007/0063; A61F 2007/0095; A61F 2007/0219; A61F 2007/0238; A61F 2007/101; A61F 5/34; A61H 7/001
See application file for complete search history.

(56) References Cited

U.S. PATENT DOCUMENTS

| | | | |
|---|---|---|---|
| 4,190,054 A | | 2/1980 | Brennan |
| 5,466,214 A | * | 11/1995 | Calderon-Garciduenas ............... A61F 5/026 128/DIG. 19 |
| 6,149,617 A | * | 11/2000 | McNally ............... A61F 13/108 602/2 |
| 6,165,147 A | * | 12/2000 | Morrow .................. A61F 5/028 602/13 |
| 6,772,439 B1 | | 8/2004 | McMullen, Jr. |
| 7,201,728 B2 | | 4/2007 | Sterling |
| 7,662,121 B2 | * | 2/2010 | Zours ..................... A61F 5/026 128/96.1 |

(Continued)

OTHER PUBLICATIONS

Hot or Cold Cherry-Pit Eye Mask, https://www.amazon.com/, 5 pages, Accessed Sep. 29, 2016.

(Continued)

*Primary Examiner* — Ophelia A Hawthorne
(74) *Attorney, Agent, or Firm* — Michael J. Feigin, Esq.; Feigin and Fridman LLC (57) ABSTRACT

A brace for treating a portion of a human body, the brace including a brace body including at least one fastener adapted for fastening the brace about the portion of the human body, and an aromatherapy heat-treatment pack removably attachable to the brace body, the aromatherapy heat-treatment pack containing at least one temperature maintaining component and at least one aromatherapeutic component, wherein the aromatherapy heat-treatment pack is adapted to maintain a temperature thereof for a predetermined treatment duration.

19 Claims, 8 Drawing Sheets

(56) References Cited

U.S. PATENT DOCUMENTS

| | | | |
|---|---|---|---|
| 2008/0064996 A1* | 3/2008 | Bretl | A61F 7/02 |
| | | | 602/21 |
| 2008/0193393 A1 | 8/2008 | Dayan | |
| 2014/0046232 A1* | 2/2014 | Sham | A61N 2/002 |
| | | | 602/2 |
| 2016/0374851 A1* | 12/2016 | Smith | A61F 7/02 |
| | | | 607/114 |

OTHER PUBLICATIONS

Cherry-Pit-Pack-What-is-it, http://www.ebay.com/gds, 3 pages, Accessed Sep. 16, 2016.
Cherry-Pit-Pac Heating Pad, www.cherrypitpac.com, 4 pages, Accessed Sep. 16, 2016.
MyPurMist Eucalyptus & Peppermint ScentPad, http://www.target.com, 2 pages, Accessed Sep. 16, 2016.
Aromatherapy Essential Oils, wvvw.cherrypitpac.com, 2 pages, Accessed Sep. 29, 2016.

* cited by examiner

BRACE WITH REMOVABLE AROMATHERAPY POUCH

FIELD OF THE DISCLOSED TECHNOLOGY

The disclosed technology relates generally to orthopedic braces, and more specifically to orthopedic braces with a removable pouch including aroma-therapeutic substances.

BACKGROUND OF THE DISCLOSED TECHNOLOGY

In many instances, such as following an injury or surgery, or to prevent injury, an orthopedic brace is used on a suitable body portion. Orthopedic braces are known in the art for many body parts, such as knees, back, neck, and elbow, and for many types of conditions.

U.S. Pat. No. 7,201,728 to Sterling describes an anatomically designed orthopedic knee brace used for treatment and rehabilitation following surgery to the knee, protection to a surgically repaired knee, and protection for an uninjured knee.

U.S. Pat. No. 6,772,439 to McMullen describes a retractable sports padding protecting the user's lower back and spine, hips, and buttocks region.

U.S. Pat. No. 4,190,054 to Brennan describes a removable bandage attachable to a body part for entirely covering the body part, the bandage being elastic so as to hold the flesh of the body part firmly in place following surgery, and may include an envelope having a heatable and/or coolable fluid therein so that the envelope may function as a hot or cold pack.

Due to the impact of temperature on the muscles, sore muscles and various pains are often treated with hot or cold packs, applied to the sore or painful area for a suitable duration. Often, such hot or cold packs include a temperature retaining substance, so as to ensure that the pack maintains a suitable temperature for the treatment duration, which is typically 20-30 minutes.

For example, Cherry Blossom Enterprises sell a Cherry-Pit-Pack microwave heating pad which is a heatable and coolable pad having cherry pits therein, which cherry pits maintain the elevated or reduced temperature (see, at the time of this wring and available in the file history for this matter at the U.S. Patent Office https://www.cherrypitpac.com/).

Aromatherapy uses plant materials and aromatic plant oils, including essential oils, and other aroma compounds, for improving one's mood, cognitive, psychological, or physical wellbeing. For example, eucalyptus leaves and eucalyptus essential oil are known for many health benefits, such as being anti-inflammatory, antispasmodic, decongestant, deodorant, antiseptic, and antibacterial.

However, the existing orthopedic braces do not combine the benefits of a brace with those of a heat/cool pack and/or of aromatherapy.

SUMMARY OF THE DISCLOSED TECHNOLOGY

The disclosed technology relates generally to orthopedic braces, and more specifically to orthopedic braces with a removable pouch including aroma-therapeutic substances.

In accordance with some aspects of an embodiment of the teachings herein, there is provided a brace for treating a portion of a human body, the brace including:

a brace body including at least one fastener adapted for fastening the brace about the portion of the human body; and an aromatherapy heat or cool treatment pack removably attached to the brace body, the aromatherapy heat or cool treatment pack including at least one temperature maintaining component and at least one aromatherapeutic component, wherein the aromatherapy heat or cool treatment pack is adapted to maintain a temperature different than an ambient temperature for a predetermined treatment duration.

In some embodiments, the at least one temperature maintaining component includes cherry pits.

In some embodiments, the at least one aromatherapeutic component includes at least one of eucalyptus leaves and eucalyptus oil.

In some embodiments, during the treatment duration, a difference between a temperature of the aromatherapy heat or cool treatment pack and a temperature of the brace body is at least 10 degrees Celsius.

In some embodiments, during the treatment duration, a difference between a temperature of the aromatherapy heat or cool treatment pack and an ambient temperature surrounding the brace body is at least 10 degrees Celsius.

In some embodiments, the brace further includes heat pack fasteners mounted onto the brace body and adapted for removable attachment of the aromatherapy heat-treatment pack to the brace body.

In some embodiments, the brace is adapted for treatment of an ankle, and wherein the brace body includes:

a main body portion;

a pair of leg surrounding extensions extending outwardly from either side of the main body portion at a first half thereof, the leg surrounding extensions including a first set of fasteners at ends thereof;

a pair of foot surrounding extensions extending outwardly from either side of the main body portion at a second half thereof, the foot surrounding extensions including a second set of fasteners at ends thereof; and a heel receiving opening disposed in the main body portion, wherein, when the brace is worn by a user, a heel of the user is received in the heel receiving opening, the first set of fasteners are fastened such that the leg surrounding extensions surround the user's leg above the heel, and the second the of fasteners are fastened such that the foot surrounding extensions surround the user's foot.

In some embodiments, the aromatherapy heat-treatment pack has an outline corresponding to that of the brace body, and includes a second heel receiving opening adapted to be aligned with the heel receiving opening.

In some embodiments, the brace is adapted for treatment of an elbow, and wherein the brace body includes:

a main body portion;

a first extension extending outwardly from one side of the main body portion at a first half thereof, the first extension including a first fastener at an end thereof; and a second extension extending outwardly from another side of the main body portion at a second half thereof, the second extension including a second fastener at an end thereof, wherein, when the brace is worn by a user, an elbow of the user is disposed in the main body portion, the first fastener is fastened to the main body portion such that the first extension surrounds the user's arm above the elbow, and the second fastener is fastened to the main body portion such that the second extension surrounds the user's arm below the elbow.

In some embodiments, the brace is adapted for treatment of a knee, and wherein the brace body includes:

a main body portion including a first pair of fasteners on opposite sides of the main body portion at a middle section thereof;

a first extension extending outwardly from one of the opposite sides of the main body portion at an upper section thereof, the first extension including a second fastener at an end thereof;

a second extension extending outwardly from another of the opposite sides of the main body portion at a lower section thereof, the second extension including a third fastener at an end thereof; and a kneecap receiving opening at a center of the main body portion, wherein, when the brace is worn by a user, a kneecap of the user is disposed in the kneecap receiving opening, the opposite sides of the main body portion are fastened to each other using the first pair of fasteners, the second fastener is fastened to the main body portion such that the first extension surrounds the user's leg above the knee, and the third fastener is fastened to the main body portion such that the second extension surrounds the user's arm below the knee.

In some embodiments, the brace is adapted for spinal treatment, and wherein the brace body includes:

an elongate torso strap including torso strap fasteners at either end thereof; and a spinal strap, one end thereof extending away from the torso strap and the other end thereof including a pair of shoulder straps terminating in shoulder strap fasteners, wherein, when the brace is worn by a user, the torso strap is fastened onto the user's torso using the torso strap fasteners, and the spinal strap extends along a spine of the user such that the shoulder straps extend over shoulders of the user and are fastened to the torso strap, at a side thereof opposite the spinal strap, by the shoulder strap fasteners.

In some embodiments, the spinal strap is removably attached to the torso strap.

In accordance with some aspects of another embodiment of the teachings herein, there is provided a method of providing treatment and support to a body portion of a user using the brace described above, the method including the following steps, in order:

changing a temperature of the aromatherapy heat-treatment pack by at least 10 degrees Celsius;

attaching the aromatherapy heat-treatment pack to the brace body; and placing the brace body on the body portion of the user such that the aromatherapy heat-treatment pack faces or engages skin of the body portion of the user.

In some embodiments, the method further includes maintaining the brace on the body portion of the user for the predetermined treatment duration.

Any device or step to a method described in this disclosure can comprise or consist of that which it is a part of, or the parts which make up the device or step. The term "and/or" is inclusive of the items which it joins linguistically and each item by itself.

DETAILED DESCRIPTION OF EMBODIMENTS OF THE DISCLOSED TECHNOLOGY

The disclosed technology relates generally to orthopedic braces, and more specifically to orthopedic braces with a removable pouch including aroma-therapeutic substances.

Figure 1A:
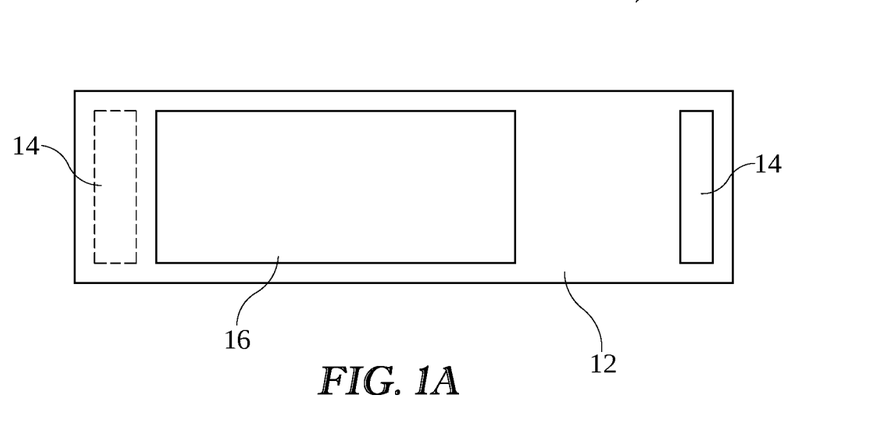
FIGS. 1A and 1B are schematic illustrations of an embodiment of an all-purpose aromatherapy-heat-pack brace in accordance with the teachings herein, in aromatherapy-heat-pack attached and detached modes, respectively.
Figure 1B:
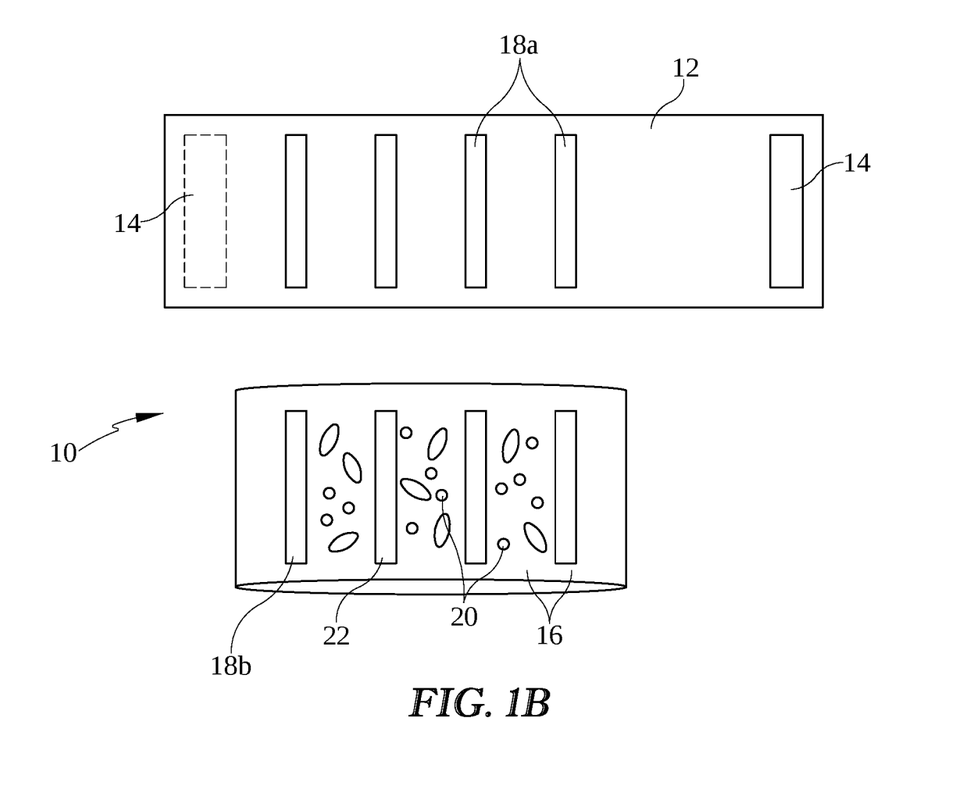

Reference is now made to FIGS. 1A and 1B, which are schematic illustrations of an embodiment of an all-purpose aromatherapy-heat-pack brace in accordance with the teachings herein, in aromatherapy-heat-pack attached and detached modes, respectively.

As seen, an all-purpose aromatherapy-heat-pack brace 10 is a generally elongate brace body 12 formed of an elastic material such as neoprene or a rigid plastic in other embodiments. At either end thereof, brace body 12 includes fasteners 14 for fastening the brace onto the body. In some embodiments, the fasteners may be corresponding Velcro® portions, corresponding halves of snaps, buttons and corresponding button loops, hooks and corresponding eyes, or any other suitable type of fasteners.

An aromatherapy heat/cold pack 16 is mounted onto an interior surface of brace body 12, for example by means of fasteners 18a attached to brace body 12 and corresponding fasteners 18b attached to pack 16, both of which are clearly seen in FIG. 1B. Typically, as seen in FIG. 1B, fasteners 18a and 18b include corresponding Velcro® strips. However, any other suitable kind of fasteners, such as snaps, hook and eye fasteners, buttons and button-holes, and the like, are considered within the scope of the disclosed technology.

As seen in the schematic illustration of heat pack 16 in FIG. 1B, heat pack 16 includes cherry pits 20 adapted to maintain a temperature of the heat-pack for a suitable duration, such as 30 minutes, as well as eucalyptus leaves 22 and/or eucalyptus oil adapted to provide aromatherapy treatment to the muscles on which the brace is applied, as known in the art of aromatherapy. The cherry pits or eucalyptus leaves can first be placed in an enclosed bag or sack, such as one made out of cotton.

Figure 11:
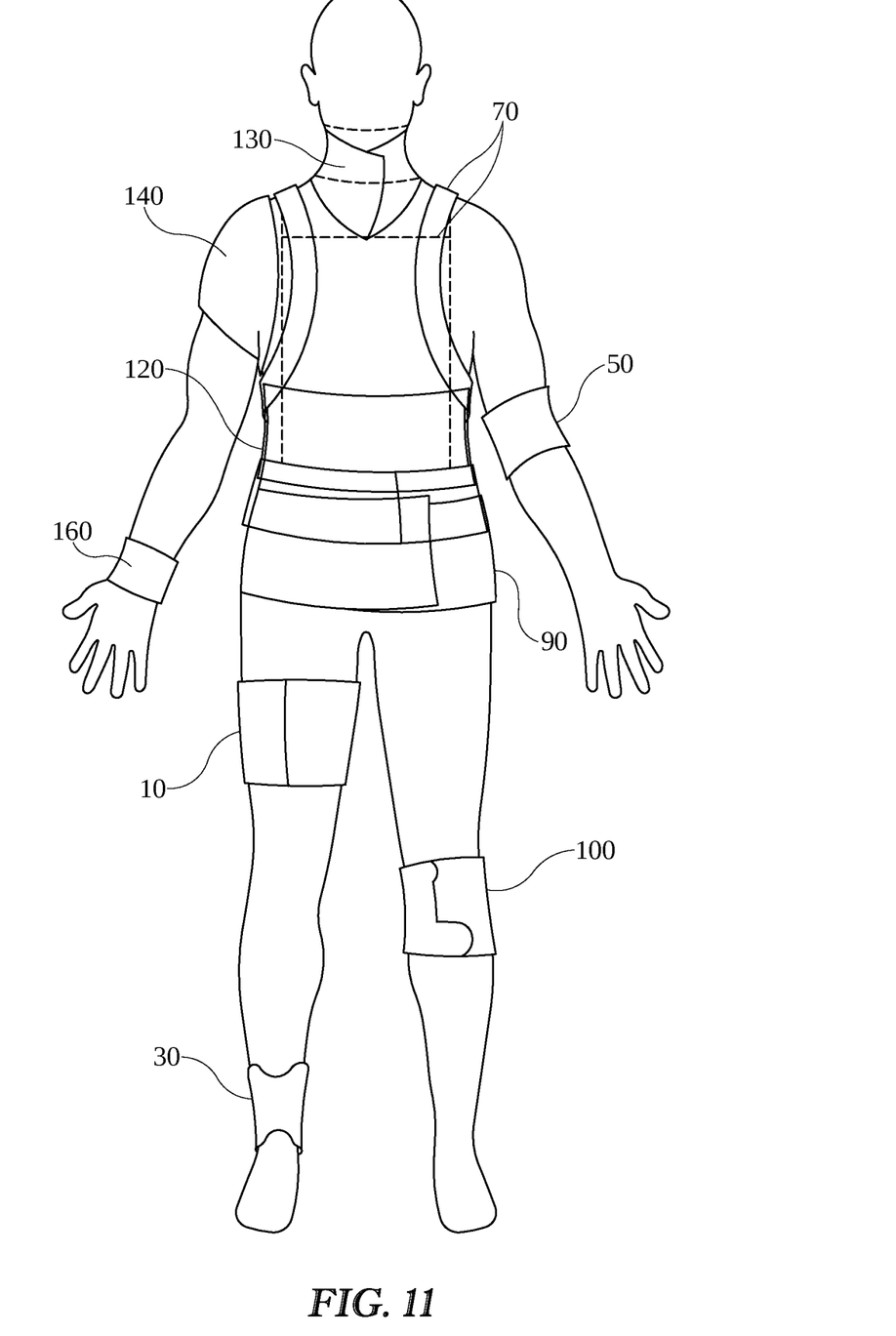
FIG. 11 is a schematic illustration of places where the braces of FIGS. 1A to 10 are placed on the body, in embodiments of the disclosed technology.

In use, the aromatherapy heat/cold pack 16 is removed from brace body 12 and is subjected to heating or cooling, as required, until the temperature of the heat pack 16 changes by at least 10 degrees Celsius from room temperature or from its initial temperature. The heated/cooled pack 16 is then attached to brace body 12 using fasteners 18*a* and 18*b*, as shown in FIG. 1A, and is fastened to an appropriate portion of the user's body, with pack 16 facing the skin surface of the user's body, using fasteners 14. For example, FIG. 11 shows the all-purpose aromatherapy-heat-pack brace 10 of FIGS. 1A and 1B applied to the shin of a user, so as to apply heat therapy and aromatherapy to the Gastrocnemius muscle of the user. The brace 10 including heat pack 16 is maintained on the user's body for a predetermined treatment duration, which is typically at least 5 minutes, at least 10 minutes, at least 20 minutes, or at least 30 minutes.

Figure 2:
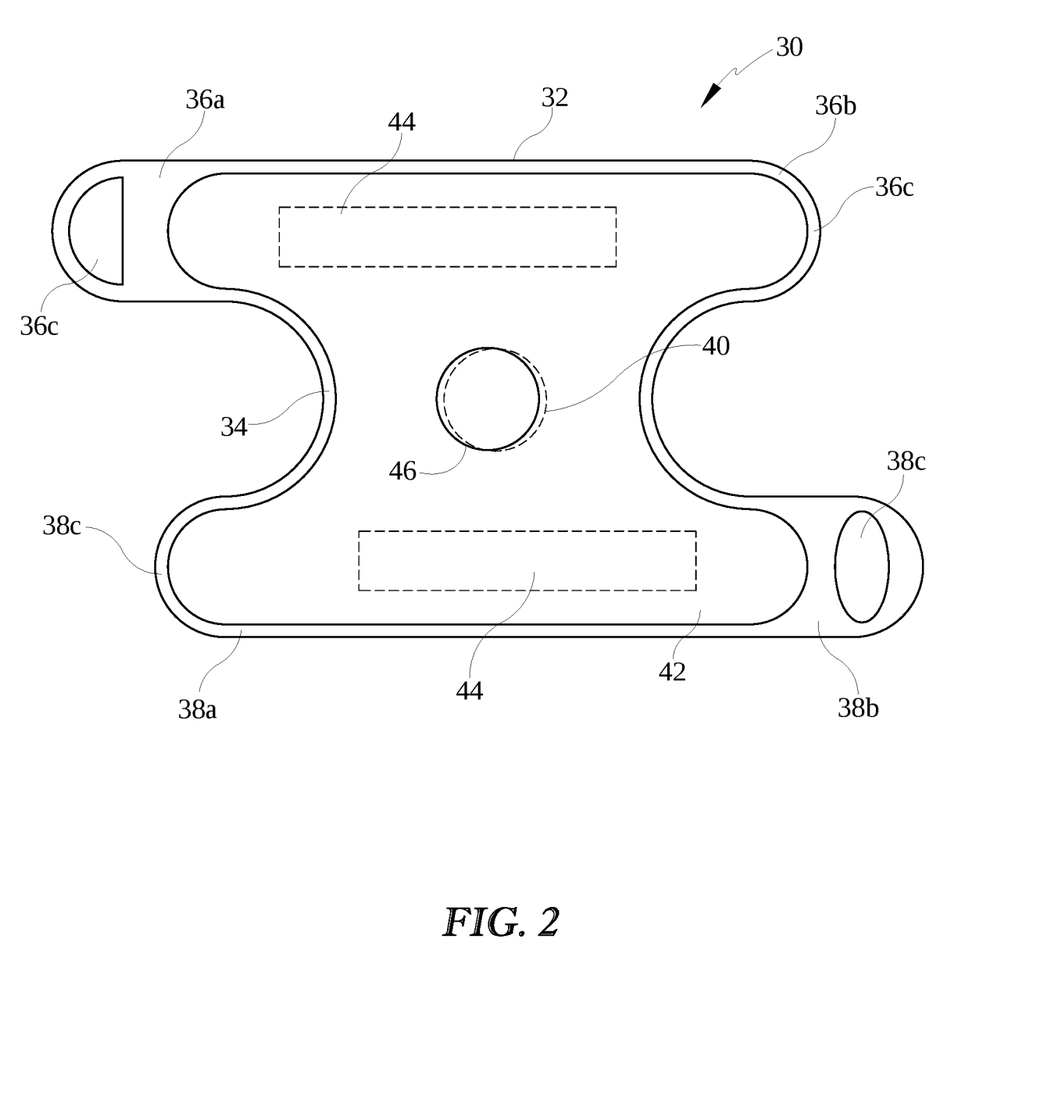
FIG. 2 is a schematic illustration of an embodiment of an ankle aromatherapy-heat-pack brace in accordance with the teachings herein, in an aromatherapy-heat-pack attached mode.

Reference is now made to FIG. 2, which is a schematic illustration of an embodiment of an ankle aromatherapy-heat-pack brace in accordance with the teachings herein, in an aromatherapy-heat-pack attached mode.

As seen, ankle brace 30 includes an ankle brace body 32, including main portion 34 from which extend two foot surrounding extensions 36*a* and 36*b*, and two leg surrounding extensions 38*a* and 38*b*. Foot surrounding extensions 36*a* and 36*b* are adapted to be connected to one another using fasteners 36*c*, and leg surrounding extensions 38*a* and 38*b* are adapted to be connected to one another using fasteners 38*c*. In the center of main portion 34 there is a heel receiving opening 40, adapted to receive the user's heel, when the ankle brace 30 is in use by a user, as seen in FIG. 11. The ankle brace is suitably sized to receive the user's ankle and provide support thereto, and the fasteners may be constructed so as to enable adjustable sizing.

An aromatherapy heat/cold pack 42 including cherry pits as well as eucalyptus leaves and/or eucalyptus oil, similar to heat pack 16 of FIGS. 1A and 1B, is removably attached to the inner surface of ankle brace body 32 by fasteners 44, substantially as described hereinabove with reference to FIGS. 1A and 1B. As seen in FIG. 2, heat pack 42 may have a contour substantially similar to that of main brace body 32, and a includes a heel receiving opening 44 corresponding in location to heel receiving opening 40 of brace body 32. However, in some embodiments, heat pack 42 may cover only a portion of brace body 30, such as covering only main portion 34, or only one half of the brace body such as extensions 36*a* and 36*b* and the part of main portion 34 connecting those two extension.

Use of ankle brace 30 is substantially similar to that of all-purpose brace 10. Heat pack 42 is removed from the main brace body 32 for heating or cooling thereof as described hereinabove with reference to FIGS. 1A and 1B, and is subsequently reconnected to main brace body 32 using the fasteners 44. The heel of the user's foot is then placed in the heel receiving openings 40 and 44 such that heat pack 42 faces or engages the user's skin, following which foot surrounding extensions 36*a* and 36*b* are fastened around the user's foot using fasteners 36*c*, and leg surrounding extensions 38*a* and 38*b* are fastened around the user's leg using fasteners 38*c*. The brace 30 is maintained on the user's ankle for a suitable treatment period, substantially as described hereinabove.

Figure 3:
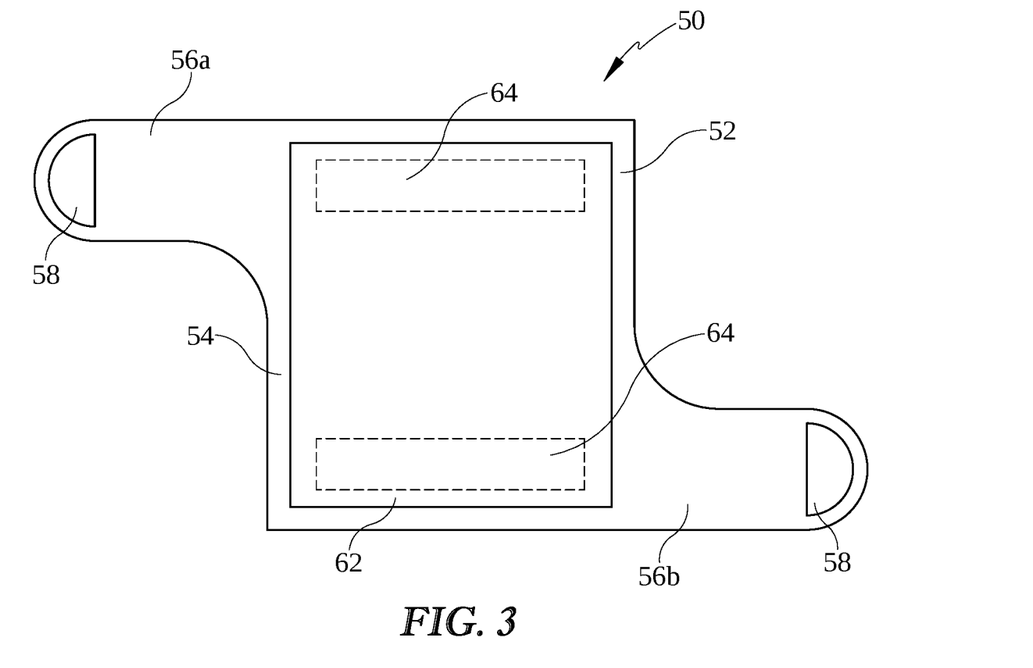
FIG. 3 is a schematic illustration of an embodiment of an elbow aromatherapy-heat-pack brace in accordance with the teachings herein, in an aromatherapy-heat-pack attached mode.

Reference is now made to FIG. 3, which is a schematic illustration of an embodiment of an elbow aromatherapy-heat-pack brace in accordance with the teachings herein, in an aromatherapy-heat-pack attached mode.

As seen, elbow brace 50 includes an elbow brace body 52, including main portion 54 from which extend two extensions 56*a* and 56*b*. Extensions 56*a* and 56*b* are adapted to be connected to main portion 54 on opposite sides thereof, using fasteners 58. Elbow brace 50 is adapted to be worn on a user's elbow, as seen in FIG. 11. The elbow brace is suitably sized to receive the user's elbow and provide support thereto, and the fasteners may be constructed so as to enable adjustable sizing.

An aromatherapy heat/cold pack 62 including cherry pits as well as eucalyptus leaves and/or eucalyptus oil, similar to heat pack 16 of FIGS. 1A and 1B, is removably attached to the inner surface of ankle brace body 52 by fasteners 64, substantially as described hereinabove with reference to FIGS. 1A and 1B. As seen in FIG. 3, heat pack 62 covers only main portion 54 of brace body 52, though in some embodiments heat pack 62 may correspond in shape to the entirety of brace body 52.

Use of elbow brace 50 is substantially similar to that of all-purpose brace 10. Heat pack 62 is removed from the main brace body 52 for heating or cooling thereof as described hereinabove with reference to FIGS. 1A and 1B, and is subsequently reconnected to main brace body 52 using the fasteners 64. The user's elbow is then placed in the center of body portion 54 such that heat pack 62 faces or engages the user's skin, following which extensions 56*a* and 56*b* are fastened around the user's arm on either side of the elbow using fasteners 58. The brace 50 is maintained on the user's elbow for a suitable treatment period, substantially as described hereinabove.

Figure 4:
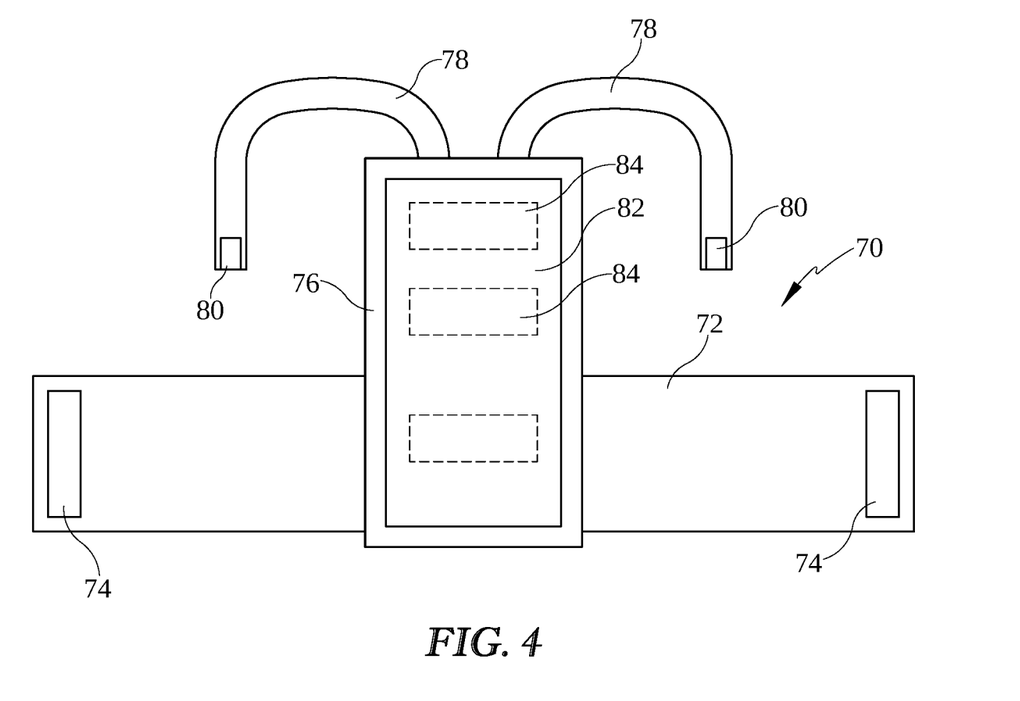
FIG. 4 is a schematic illustration of an embodiment of a full-back aromatherapy-heat-pack brace in accordance with the teachings herein, in an aromatherapy-heat-pack attached mode.

Reference is now made to FIG. 4, which is a schematic illustration of an embodiment of a full-back aromatherapy-heat-pack brace in accordance with the teachings herein, in an aromatherapy-heat-pack attached mode.

As seen, full-back brace 70 includes an elongate torso strap 72 adapted to be worn about the torso of a user and to be fastened thereabout with fasteners 74. Extending outwardly from torso strap 72 is a spinal strap 76, terminating in two shoulder strap 78, which may be elastic and are adapted to attach to torso strap 72 on an opposite side thereof using suitable fasteners 80. As such, when a user wears brace 70, as shown in FIG. 11, torso strap 72 surrounds the user's torso such that spinal strap 76 extends along the user's spine, and shoulder straps 78 extend over the user's shoulders and connect back to the torso strap 72 at the front of the user's body, in a manner similar to suspenders. The brace is suitably sized to fit around the user's torso and back and to provide support thereto, and the fasteners may be constructed so as to enable adjustable sizing.

In some embodiments, torso strap 72 and spinal strap 76 may be formed of two separate pieces, permanently connected to one another, for example by sewing the two straps together, or removably or adjustably connected to one another, such as by fasteners, or by threading torso strap 72 through a suitable slot in spinal strap 76. In some such embodiments the torso strap 72 and spinal strap 76 may be formed of distinct materials, such as torso strap 72 being elastic to accommodate different torso girths, whereas spinal strap 76 may be more rigid to provide some structural support to the spine. In other embodiments, torso strap 72 and spinal strap 76 may be integrally formed, for example from a single piece of fabric, and/or may be formed of the same material.

An aromatherapy heat/cold pack 82 including cherry pits as well as eucalyptus leaves and/or eucalyptus oil, similar to heat pack 16 of FIGS. 1A and 1B, is removably attached to the inner surface of spinal strap 76 by fasteners 84, substantially as described hereinabove with reference to FIGS. 1A and 1B. As seen in FIG. 4, heat pack 82 covers at least the majority of the spinal strap 76. However, in some embodiments, heat pack 82, or one or more second heat packs (not shown) may also be disposed along an inner surface of torso strap 72.

Use of full-back brace 70 is substantially similar to that of all-purpose brace 10. Heat pack 82 is removed from the spinal strap 76 for heating or cooling thereof as described hereinabove with reference to FIGS. 1A and 1B, and is subsequently reconnected to spinal strap 76 using the fasteners 84. The user then fastens torso strap 72 about their torso using fasteners 74, such that spinal strap 76 is aligned with the user's spine. The user then places spinal strap 76 along his/her spine such that heat pack 82 faces or engages the user's skin and shoulder straps 78 extend over the user's shoulders, and attaches shoulder straps 78 to torso strap 72 at the front side of the user's body using fasteners 80. The brace 70 is maintained on the user's torso and spine for a suitable treatment period, substantially as described hereinabove.

Figure 5:
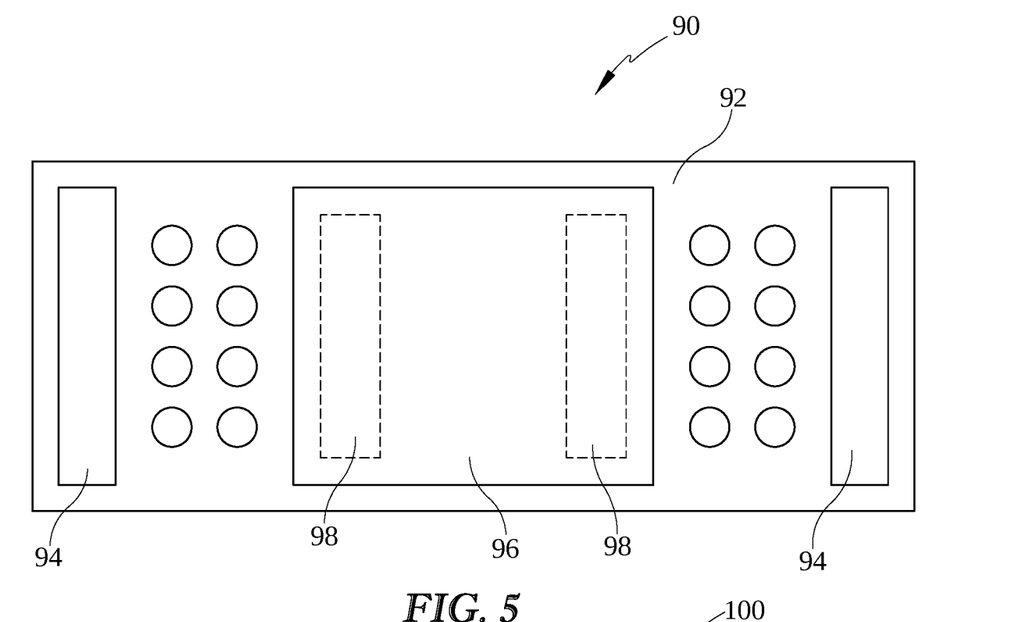
FIG. 5 is a schematic illustration of an embodiment of a hip aromatherapy-heat-pack brace in accordance with the teachings herein, in an aromatherapy-heat-pack attached mode.

Reference is now made to FIG. 5, which is a schematic illustration of an embodiment of a hip aromatherapy-heat-pack brace in accordance with the teachings herein, in an aromatherapy-heat-pack attached mode.

As seen, hip brace 90 includes an elongate hip brace body 92 terminating on either side thereof in fasteners 94. As seen in FIG. 11, when hip brace 90 is in use by the user, brace body 92 is disposed about the user's hips and fastened thereabout by fasteners 94. The hip brace is suitably sized to receive the user's hips and provide support thereto, and the fasteners may be constructed so as to enable adjustable sizing.

An aromatherapy heat/cold pack 96 including cherry pits as well as eucalyptus leaves and/or eucalyptus oil, similar to heat pack 16 of FIGS. 1A and 1B, is removably attached to the inner surface of hip brace body 92 by fasteners 98, substantially as described hereinabove with reference to FIGS. 1A and 1B. As seen in FIG. 5, heat pack 96 is sized to cover only a portion of the length of hip brace body 92, though it is appreciated that it may also be sized to cover the entire hip brace body.

Use of hip brace 90 is substantially similar to that of all-purpose brace 10. Heat pack 96 is removed from the main brace body 92 for heating or cooling thereof as described hereinabove with reference to FIGS. 1A and 1B, and is subsequently reconnected to main brace body 92 using the fasteners 98. The brace body is then fastened around the user's hips with fasteners 94, such that heat pack 96 faces or engages the user's skin. The brace 90 is maintained on the user's hips for a suitable treatment period, substantially as described hereinabove.

Figure 6:
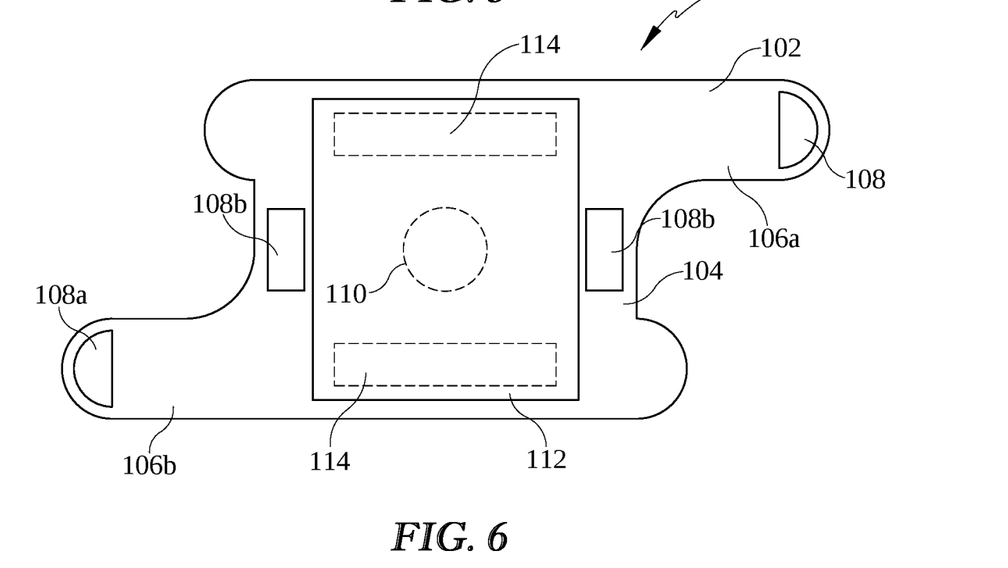
FIG. 6 is a schematic illustration of an embodiment of a knee aromatherapy-heat-pack brace in accordance with the teachings herein, in an aromatherapy-heat-pack attached mode.

Reference is now made to FIG. 6, which is a schematic illustration of an embodiment of a knee aromatherapy-heat-pack brace in accordance with the teachings herein, in an aromatherapy-heat-pack attached mode.

As seen, knee brace 100 includes a knee brace body 102, including main portion 104 from which extend two extensions 106a and 106b. Extensions 106a and 106b are adapted to be connected to main portion 104 on opposite sides thereof, using fasteners 108a. Additional fasteners 108b, disposed generally at the center of main portion 104, are adapted to connect opposite attach opposite sides of main portion 104 to each other. In some embodiments, main portion 104 includes a central opening 110, adapted to receive the knee cap and to allow more flexible motion of the user's knee while wearing brace 100. Knee brace 100 is adapted to be worn on a user's knee, as seen in FIG. 11. The knee brace is suitably sized to receive the user's knee and provide support thereto, and the fasteners may be constructed so as to enable adjustable sizing.

An aromatherapy heat/cold pack 112 including cherry pits as well as eucalyptus leaves and/or eucalyptus oil, similar to heat pack 16 of FIGS. 1A and 1B, is removably attached to the inner surface of knee brace body 102 by fasteners 114, substantially as described hereinabove with reference to FIGS. 1A and 1B. As seen in FIG. 6, heat pack 112 covers only main portion 104 of brace body 102, though in some embodiments heat pack 112 may correspond in shape to the entirety of brace body 102.

Use of knee brace 100 is substantially similar to that of all-purpose brace 10. Heat pack 112 is removed from the main brace body 102 for heating or cooling thereof as described hereinabove with reference to FIGS. 1A and 1B, and is subsequently reconnected to main brace body 102 using the fasteners 114. The user's knee is then placed in the center of body portion 104 such that heat pack 112 faces or engages the user's skin, following which extensions 106a and 106b are fastened around the user's leg on either side of the knee using fasteners 108a, and sides of body portion 104 are fastened at the back of the user's knee using fasteners 108b. The brace 100 is maintained on the user's knee for a suitable treatment period, substantially as described hereinabove.

Figure 7:
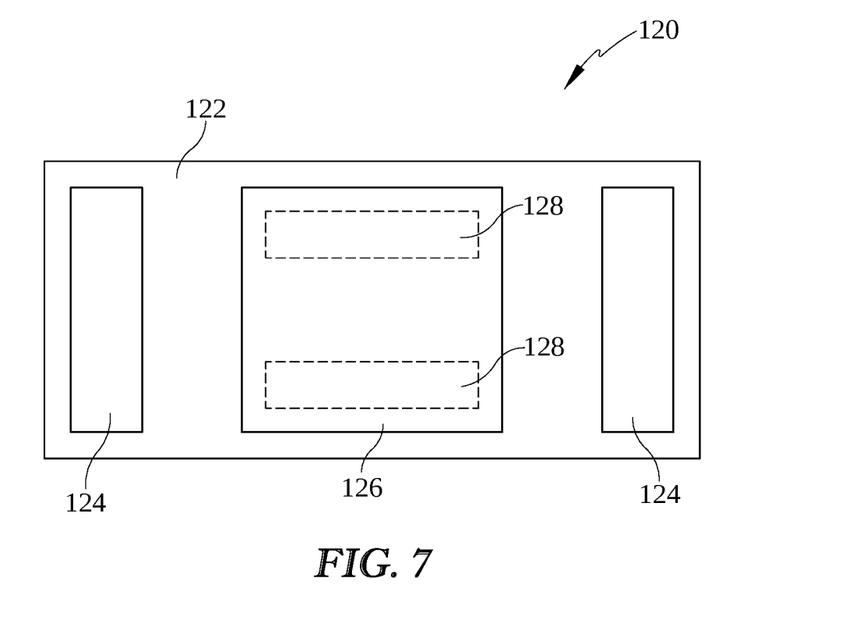
FIG. 7 is a schematic illustration of an embodiment of a lower-back aromatherapy-heat-pack brace in accordance with the teachings herein, in an aromatherapy-heat-pack attached mode.

Reference is now made to FIG. 7, which is a schematic illustration of an embodiment of a lower-back aromatherapy-heat-pack brace in accordance with the teachings herein, in an aromatherapy-heat-pack attached mode.

As seen, lower-back brace 120 includes an elongate lower-back brace body 122 terminating on either side thereof in fasteners 124. As seen in FIG. 11, when lower-back brace 120 is in use by the user, brace body 122 is disposed about the user's lower back and is fastened thereabout by fasteners 124. The lower-back brace is suitably sized to receive the user's lower back and provide support thereto, and the fasteners may be constructed so as to enable adjustable sizing.

An aromatherapy heat/cold pack 126 including cherry pits as well as eucalyptus leaves and/or eucalyptus oil, similar to heat pack 16 of FIGS. 1A and 1B, is removably attached to the inner surface of lower-back brace body 122 by fasteners 128, substantially as described hereinabove with reference to FIGS. 1A and 1B. As seen in FIG. 7, heat pack 126 is sized to cover only a portion of the length of lower-back brace body 122, though it is appreciated that it may also be sized to cover the entire lower-back brace body.

Use of lower-back brace 120 is substantially similar to that of all-purpose brace 10. Heat pack 126 is removed from the brace body 122 for heating or cooling thereof as described hereinabove with reference to FIGS. 1A and 1B, and is subsequently reconnected to brace body 122 using the fasteners 128. The brace body is then fastened around the user's lower back with fasteners 124, such that heat pack 126 faces or engages the user's skin. The brace 120 is maintained on the user's lower-back for a suitable treatment period, substantially as described hereinabove.

Figure 8:
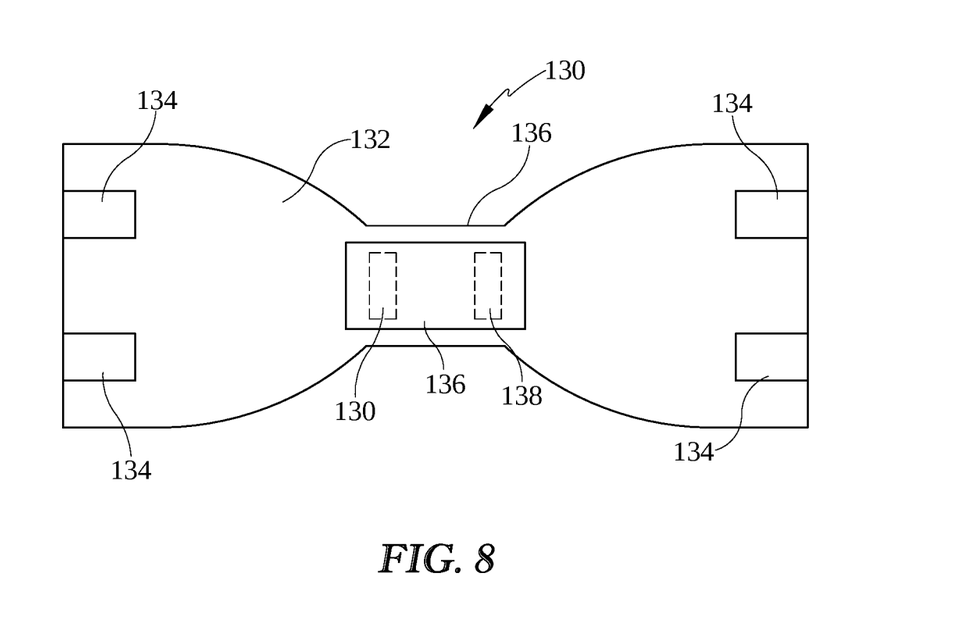
FIG. 8 is a schematic illustration of an embodiment of a neck aromatherapy-heat-pack brace in accordance with the teachings herein, in an aromatherapy-heat-pack attached mode.

Reference is now made to FIG. 8, which is a schematic illustration of an embodiment of a neck aromatherapy-heat-pack brace in accordance with the teachings herein, in an aromatherapy-heat-pack attached mode.

As seen, neck brace 130 includes an elongate neck brace body 132 terminating on either side thereof in fasteners 134, and having a narrowed portion 135 at the center thereof, such that when fasteners 134 are open, the brace body 132 has a shape similar to that of a bow. As seen in FIG. 11, when neck brace 130 is in use by the user, brace body 132 is disposed about the user's neck and is fastened thereabout by fasteners 134. The neck brace is suitably sized to be disposed about the user's neck and provide support thereto, and the fasteners may be constructed so as to enable adjustable sizing.

An aromatherapy heat/cold pack 136 including cherry pits as well as eucalyptus leaves and/or eucalyptus oil, similar to heat pack 16 of FIGS. 1A and 1B, is removably attached to the inner surface of neck brace body 132 by fasteners 138, substantially as described hereinabove with reference to FIGS. 1A and 1B. As seen in FIG. 8, in some embodiments heat pack 136 is sized to cover only or substantially only narrowed portion 135 of neck brace body 132, though it is appreciated that it may also be sized to cover the entire neck brace body.

Use of neck brace 130 is substantially similar to that of all-purpose brace 10. Heat pack 136 is removed from the brace body 132 for heating or cooling thereof as described hereinabove with reference to FIGS. 1A and 1B, and is subsequently reconnected to brace body 132 using the fasteners 138. The brace body is then fastened around the user's neck with fasteners 134, such that heat pack 136 faces or engages the user's skin. The brace 130 is maintained on the user's neck for a suitable treatment period, substantially as described hereinabove.

Figure 9:
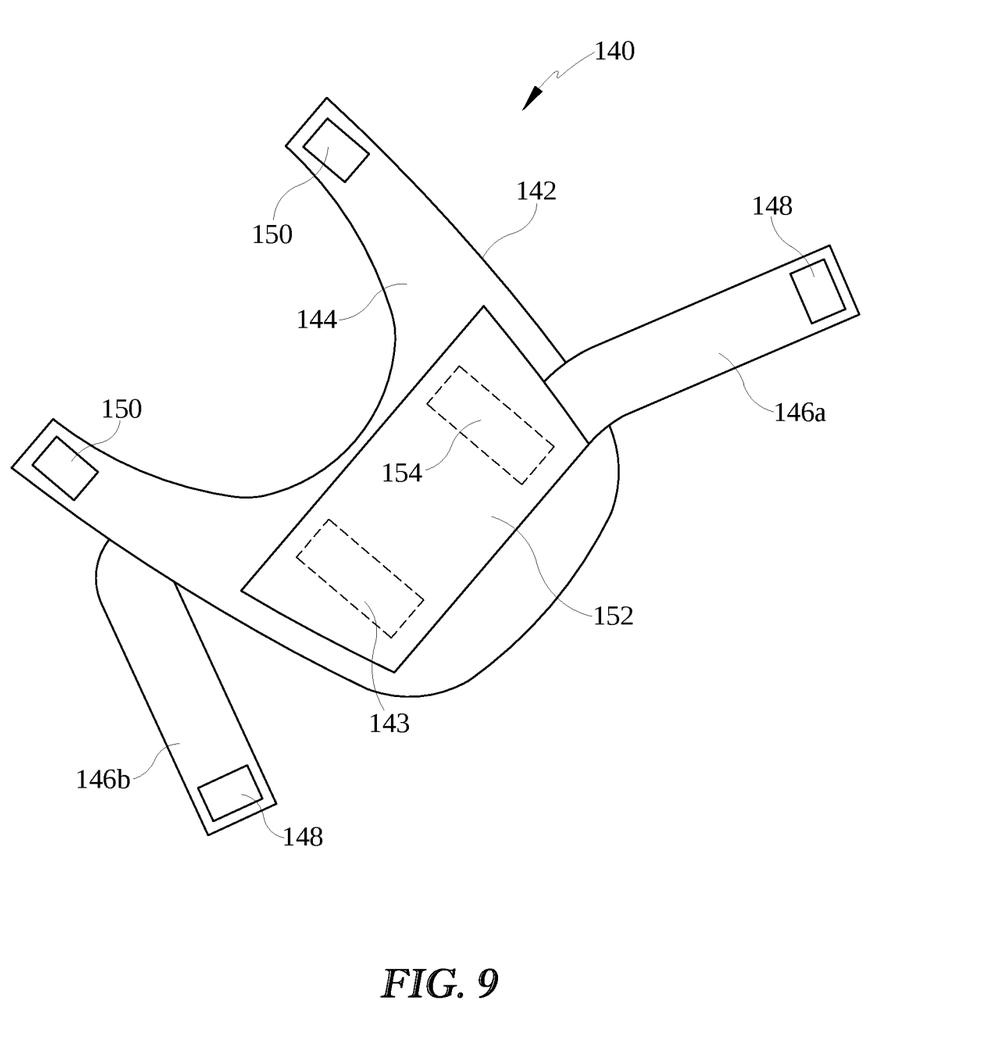
FIG. 9 is a schematic illustration of an embodiment of a shoulder aromatherapy-heat-pack brace in accordance with the teachings herein, in an aromatherapy-heat-pack attached mode.

FIG. 9 is a schematic illustration of an embodiment of a shoulder aromatherapy-heat-pack brace in accordance with the teachings herein, in an aromatherapy-heat-pack attached mode.

As seen, shoulder brace 140 includes a shoulder brace body 142, including a generally arcuate or U-shaped main portion 144. Two strapping extensions 146a and 146b extend from main portion 144, and terminate in fasteners 148. Extensions 146a and 146b are adapted to be connected to each other using fasteners 148. Additional fasteners 150, disposed at the ends of the U-shaped arms of main portion 144, are adapted to connect opposite sides of main portion 144 to each other. Shoulder brace 140 is adapted to be worn on a user's knee, as seen in FIG. 11. The shoulder brace is suitably sized to receive the user's shoulder and provide support thereto, and the fasteners may be constructed so as to enable adjustable sizing.

An aromatherapy heat/cold pack 152 including cherry pits as well as eucalyptus leaves and/or eucalyptus oil, similar to heat pack 16 of FIGS. 1A and 1B, is removably attached to the inner surface of shoulder brace body 142 by fasteners 154, substantially as described hereinabove with reference to FIGS. 1A and 1B. As seen in FIG. 9, heat pack 152 covers only the center of the U-shape of main portion 144 of brace body 142, though in some embodiments heat pack 152 may correspond in shape to the entirety of the main portion 144.

Use of shoulder brace 140 is substantially similar to that of all-purpose brace 10. Heat pack 152 is removed from the main brace body 142 for heating or cooling thereof as described hereinabove with reference to FIGS. 1A and 1B, and is subsequently reconnected to main brace body 142 using the fasteners 154. The brace is then placed on the user's shoulder such that the central portion of U-shaped main portion 144, holding heat pack 152, is placed above the user's shoulder, the arms of U-shaped main portion 144 are connected to each other by fasteners 150 at the user's underarm, and extensions 146a and 146b are connected to each other using fasteners 148 around the user's arm. The main portion 144 is placed such that heat pack 152 faces or engages the user's skin. The brace 140 is maintained on the user's shoulder for a suitable treatment period, substantially as described hereinabove.

Figure 10:
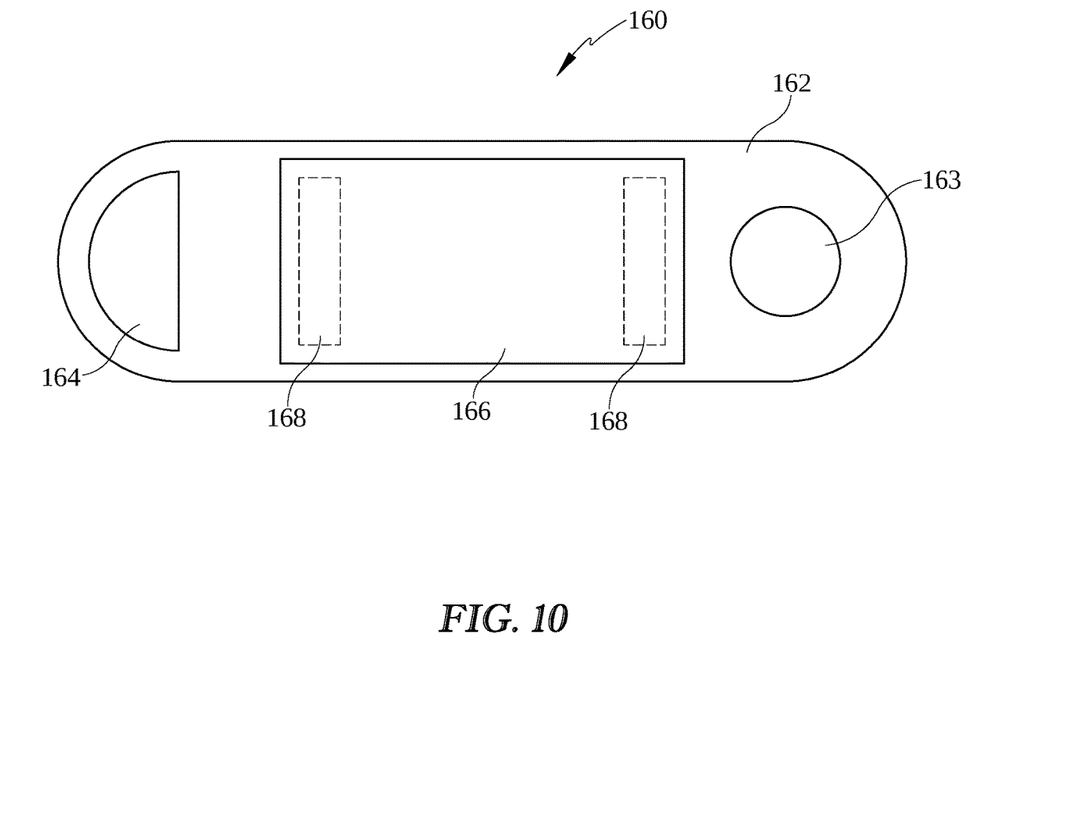
FIG. 10 is a schematic illustration of an embodiment of a wrist aromatherapy-heat-pack band in accordance with the teachings herein, in an aromatherapy-heat-pack attached mode.

FIG. 10 is a schematic illustration of an embodiment of a wrist aromatherapy-heat-pack band in accordance with the teachings herein, in an aromatherapy-heat-pack attached mode.

As seen, wrist band 160 includes an elongate wrist band body 162 including a thumb opening 163 at one end thereof and terminating, at an opposite end thereof, in a fastener 164. As seen in FIG. 11, when wrist band 160 is in use by the user, the user's thumb extends through opening 163 and the wrist band body 162 is disposed about the user's wrist and is fastened thereabout by fastener 164. The wrist band is suitably sized to be disposed about the user's wrist and provide support thereto, and the fasteners may be constructed so as to enable adjustable sizing.

An aromatherapy heat/cold pack 166 including cherry pits as well as eucalyptus leaves and/or eucalyptus oil, similar to heat pack 16 of FIGS. 1A and 1B, is removably attached to the inner surface of wrist band body 162, substantially alongside opening 163, by fasteners 168, substantially as described hereinabove with reference to FIGS. 1A and 1B. As seen in FIG. 10, in some embodiments heat pack 166 is sized to cover substantially all of wrist band body 162 other than thumb opening 163.

Use of wrist band 160 is substantially similar to that of all-purpose brace 10. Heat pack 166 is removed from the wrist band body 162 for heating or cooling thereof as described hereinabove with reference to FIGS. 1A and 1B, and is subsequently reconnected to wrist band body 162 using the fasteners 168. The user then puts his/her thumb through opening 163, and fastens the wrist band body 162 around the user's wrist with fasteners 164, such that heat pack 166 faces or engages the user's skin. The wrist band 160 is maintained on the user's neck for a suitable treatment period, substantially as described hereinabove.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described herein-above are also contemplated and within the scope of the disclosed technology.

I claim:

1. A brace for treating a portion of a human body, the brace comprising:
   a brace body including a heat pack fastener disposed on an interior surface of the brace body and a brace fastener disposed on an end of the brace body, the brace fastener configured to fasten to an end of the brace body, thereby enabling securement of the brace about a portion of a human body;

an aromatherapy heat or cool treatment pack including a plurality of aromatherapeutic components, a plurality of temperature maintaining components, and a corresponding heat pack fastener corresponding to the heat pack fastener such that the aromatherapy heat or cool treatment pack is removably attachable to the interior surface of the brace body; wherein the body brace further comprises:

a main body portion including a first end, a second end, a first side, a second side, and a first fastener including a pair of fasteners disposed on the first side and the second side, the first pair of fasteners configured to attach to each other about a knee, the first end opposing the second end and the first side opposing the second side;

a first extension extending perpendicularly outwardly from the second side of the main body portion adjacent the first end, the first extension including a second fastener disposed on an end thereof, the second fastener configured to attach to the first side of the main body portion adjacent the first end about a user's leg above the knee;

a second extension extending perpendicularly outwardly from the first side of said main body portion adjacent the second end, the second extension including a third fastener disposed on an end thereof, the third fastener configured to attach to the second side of the main body portion adjacent the second end about the user's leg below the knee; and a kneecap receiving opening cut out from a center of the main body portion, the kneecap receiving opening configured to receive a kneecap therethrough, wherein the first extension is offset relative to the second extension about a central longitudinal and central latitudinal axis of the main body portion, such that they are asymmetrical with respect to each other about a center of the main body portion.

2. The brace of claim 1, wherein the body brace further comprises:

an elongated torso strap including a torso strap fastener disposed on opposing ends thereof, the torso strap fasteners configured to fasten to each other about a user's torso;

the brace body disposed centrally along a length of the elongated torso strap, the brace body extending perpendicularly outwardly relative to the elongated torso strap and defining a spinal strap extending along a spine of the user when the elongated torso strap is mounted onto the user, a pair of shoulder straps extending outwardly from an end of the brace body that is opposite the end of the brace body attached to the elongated torso strap, each of the pair of shoulder straps including a shoulder strap fastener, the pair of shoulder straps configured to extend over the user's shoulders when the elongated torso strap is mounted onto the user, the pair of shoulder straps removably attachable to a side of the elongated torso strap that is opposite the spinal strap via the shoulder strap fasteners.

3. The brace of claim 2, wherein the spinal strap is removably attached to the torso strap.

4. The brace of claim 2, wherein:

a first end of the brace body includes the heat pack fastener for receiving the corresponding heat pack fastener of the aromatherapy heat or cool treatment pack, a second end of the brace body includes a second heat pack fastener, the aromatherapy heat or cool treatment pack includes a second corresponding heat pack fastener configured to removably attach to the second heat pack fastener, and the aromatherapy heat or cool treatment pack includes a contour substantially similar to the contour of the spinal strap.

5. The brace of claim 1, wherein the heat pack fastener of the brace body and the corresponding heat pack fasteners of the aromatherapy heat or cool treatment pack include a plurality of fastening strips disposed widthwise across a surface thereof, wherein the plurality of fastening strips of brace body and the aromatherapy heat or cool treatment pack are aligned enabling securement to each other.

6. The brace of claim 1, wherein:

the first end of the main body portion includes the heat pack fastener for receiving the corresponding heat pack fastener of the aromatherapy heat or cool treatment pack, the second end includes a second heat pack fastener, the aromatherapy heat or cool treatment pack includes a second corresponding heat pack fastener configured to removably attach to the second heat pack fastener, and the aromatherapy heat or cool treatment pack includes a contour substantially similar to the contour of the main body portion.

7. A brace for treating a portion of a human body, the brace comprising:

a brace body including a heat pack fastener disposed on an interior surface of the brace body and a brace fastener disposed on an end of the brace body, the brace fastener configured to fasten to an end of the brace body, thereby enabling securement of the brace about a portion of a human body;

an aromatherapy heat or cool treatment pack including a plurality of aromatherapeutic components, a plurality of temperature maintaining components, and a corresponding heat pack fastener corresponding to the heat pack fastener such that the aromatherapy heat or cool treatment pack is removably attachable to the interior surface of the brace body;

a main body portion including a first end and a second end, the first end opposing the second end;

a pair of leg surrounding extensions disposed on the first end of the main body portion, the pair of leg surrounding extensions extending perpendicularly outwardly relative to the main body portion, the pair of leg surrounding extensions including a first set of fasteners disposed at ends thereof, the first set of fasteners configured to attach about a user's leg for securing the pair of leg surrounding extensions therearound;

a pair of foot surrounding extensions disposed on the second end of the main body portion, the pair of foot surrounding extensions extending perpendicularly outwardly relative to the main body portion, the pair of foot surrounding extensions including a second set of fasteners disposed at ends thereof, the second set of fasteners configured to attach about a user's foot for securing the pair of foot surrounding extensions therearound; and a heel receiving opening disposed in a center of the main body portion, the heel receiving opening configured to receive a heel therethrough, wherein the pair of leg surrounding extensions are offset relative to the pair of foot surrounding extensions about a central axis of the main body, such that they are asymmetrical with respect to each other about a center of the heel receiving opening.

8. The brace of claim 7, wherein the plurality of temperature maintaining components comprise cherry pits.

9. The brace of claim 8, wherein the plurality of aromatherapeutic components comprise at least one of eucalyptus leaves and eucalyptus oil.

10. The brace of claim 7, wherein the temperature maintaining component maintains a temperature of the aromatherapy heat or cool pack for approximately 30 minutes.

11. The brace of claim 7, wherein:
the pair of leg surrounding extensions include the heat pack fastener for receiving the corresponding heat pack fastener of the aromatherapy heat or cool treatment pack,
the pair of foot surrounding extensions include a second heat pack fastener,
the aromatherapy heat or cool treatment pack includes a second corresponding heat pack fastener configured to removably attach to the second heat pack fastener, and
the aromatherapy heat or cool treatment pack includes a contour substantially similar to the contour of the brace body and includes an opening in alignment with the heel receiving opening when the aromatherapy heat or cool treatment pack is attached to the brace body.

12. A brace for treating a portion of a human body, the brace comprising:
a brace body including a heat pack fastener disposed on an interior surface of the brace body and a brace fastener disposed on an end of the brace body, the brace fastener configured to fasten to an end of the brace body, thereby enabling securement of the brace about a portion of a human body;
an aromatherapy heat or cool treatment pack including a plurality of aromatherapeutic components, a plurality of temperature maintaining components, and a corresponding heat pack fastener corresponding to the heat pack fastener such that the aromatherapy heat or cool treatment pack is removably attachable to the interior surface of the brace body;
wherein the brace body further comprises: a main body portion including a first end, a second end, a first side, and a second side, the first end opposing the second end and the first side opposing the second side;
a first extension extending perpendicularly outwardly from the first side of the main body portion adjacent the first end, the first extension including a first fastener disposed on an end thereof, the first fastener configured to attach to the second side of the main body portion adjacent the first end about a user's arm above the elbow; and
a second extension extending perpendicularly outwardly from the second side of said main body portion adjacent the second end, the second extension including a second fastener disposed on an end thereof, the second fastener configured to attach to the first side of the main body portion adjacent the second end about the user's arm below the elbow,
wherein the first extension is offset relative to the second extension about a central longitudinal and central latitudinal axis of the main body portion, such that they are asymmetrical with respect to each other about a center of the main body portion.

13. The brace of claim 12, wherein:
the first end of the main body portion includes the heat pack fastener for receiving the corresponding heat pack fastener of the aromatherapy heat or cool treatment pack,
the second end includes a second heat pack fastener,
the aromatherapy heat or cool treatment pack includes a second corresponding heat pack fastener configured to removably attach to the second heat pack fastener, and
the aromatherapy heat or cool treatment pack includes a contour substantially similar to the contour of the main body portion.

14. A method of providing treatment and support to a body portion of a user using the brace of claim 1, the method comprising the following steps, in order:
changing a temperature of the aromatherapy heat or cool treatment pack by at least 10 degrees Celsius;
attaching the aromatherapy heat or cool treatment pack to the brace body; and
placing the brace body on a body portion of the user such that the aromatherapy heat or cool treatment pack faces or engages skin of the body portion of the user.

15. The method of claim 14, further comprising maintaining the brace on the body portion of the user for a predetermined treatment duration.

16. A method of providing treatment and support to a body portion of a user using the brace of claim 7, the method comprising the following steps, in order:
changing a temperature of the aromatherapy heat or cool treatment pack by at least 10 degrees Celsius;
attaching the aromatherapy heat or cool treatment pack to the brace body;
placing the brace body on the relevant body portion of the user such that the aromatherapy heat or cool treatment pack faces or engages skin of the relevant body portion of the user; and
maintaining the brace on the body portion of the user for a predetermined treatment duration of time.

17. A method of providing treatment and support to a body portion of a user using the brace of claim 12, the method comprising the following steps, in order:
changing a temperature of the aromatherapy heat or cool treatment pack by at least 10 degrees Celsius;
attaching the aromatherapy heat or cool treatment pack to the brace body;
placing the brace body on the relevant body portion of the user such that the aromatherapy heat or cool treatment pack faces or engages skin of the relevant body portion of the user; and
maintaining the brace on the body portion of the user for a predetermined treatment duration of time.

18. A method of providing treatment and support to a body portion of a user using the brace of claim 1, the method comprising the following steps, in order:
changing a temperature of the aromatherapy heat or cool treatment pack by at least 10 degrees Celsius;
attaching the aromatherapy heat or cool treatment pack to the brace body;
placing the brace body on the relevant body portion of the user such that the aromatherapy heat or cool treatment pack faces or engages skin of the relevant body portion of the user; and
maintaining the brace on the body portion of the user for a predetermined treatment duration of time.

19. A method of providing treatment and support to a body portion of a user using the brace of claim 2, the method comprising the following steps, in order:

changing a temperature of the aromatherapy heat or cool treatment pack by at least 10 degrees Celsius;
attaching the aromatherapy heat or cool treatment pack to the brace body;
placing the brace body on the relevant body portion of the user such that the aromatherapy heat or cool treatment pack faces or engages skin of the relevant body portion of the user; and
maintaining the brace on the body portion of the user for a predetermined treatment duration of time.

* * * * *